United States Patent
Pickert

(10) Patent No.: US 10,828,005 B2
(45) Date of Patent: Nov. 10, 2020

(54) INTERACTION OF OPERATING PARAMETERS IN A MEDICAL SYSTEM

(71) Applicant: Siemens Healthcare GmbH, Erlangen (DE)

(72) Inventor: Nils Pickert, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 16/044,206

(22) Filed: Jul. 24, 2018

(65) Prior Publication Data
US 2019/0038251 A1    Feb. 7, 2019

(30) Foreign Application Priority Data
Aug. 1, 2017 (EP) .................................... 17184262

(51) Int. Cl.
| A61B 6/00 | (2006.01) |
| A61B 6/04 | (2006.01) |
| A61B 6/10 | (2006.01) |

(52) U.S. Cl.
CPC ............... *A61B 6/547* (2013.01); *A61B 6/04* (2013.01); *A61B 6/0407* (2013.01); *A61B 6/0487* (2020.08); *A61B 6/4441* (2013.01); *A61B 6/54* (2013.01); *A61B 6/542* (2013.01); *A61B 6/10* (2013.01); *A61B 6/485* (2013.01)

(58) Field of Classification Search
CPC ........ A61B 6/04; A61B 6/0407; A61B 6/0457
See application file for complete search history.

(56) References Cited

U.S. PATENT DOCUMENTS

| 2006/0109954 A1 | 5/2006 | Gohno |
| 2010/0037394 A1 | 2/2010 | Hayes |
| 2016/0113615 A1 | 4/2016 | Lee et al. |

FOREIGN PATENT DOCUMENTS

| DE | 102012215998 A1 | 3/2014 |
| DE | 102014213817 A1 * | 6/2015 |

OTHER PUBLICATIONS

European Search Report for European Patent Application No. 17184262.8-1124 dated Feb. 9, 2018.

* cited by examiner

*Primary Examiner* — Dani Fox
(74) *Attorney, Agent, or Firm* — Lempia Summerfield Katz LLC

(57) ABSTRACT

The object of the disclosure is to simplify and/or improve the operation of a medical system. To this end, a method for operating the medical system is proposed, in which a patient is moved relative to a component of the system, or the component is moved relative to the patient, according to a motion parameter. The motion parameter interacts automatically with another process parameter of the medical system so that a value of the process parameter changes dynamically with a value of the motion parameter.

17 Claims, 2 Drawing Sheets

INTERACTION OF OPERATING PARAMETERS IN A MEDICAL SYSTEM

The application claims the benefit of European Patent Application No. EP 17184262.8, filed Aug. 1, 2017, which is hereby incorporated by reference in its entirety.

TECHNICAL FIELD

The present disclosure relates to a method for operating a medical system, in which a patient is moved relative to a component of the system according to a motion parameter. The present disclosure also relates to a medical system including a component and a movement apparatus that may be used to move a patient relative to the component according to a motion parameter.

BACKGROUND

Present medical X-ray systems, which may include a patient table and an X-ray device, may use fixed parameter sets for creating images using the X-ray device and for performing movements of the patient table or of the X-ray device. The parameter sets are created by the user and not changed again during operation. If applicable, different parameter sets are used for different processes.

A C-arm X-ray device has several image parameters. These include, for instance, the dose of the X-ray radiation, the gain of the detector signals, a zoom factor for the image, and the like. The primary aim in fluoroscopy is to minimize the X-ray dose for the patient and also for the operating personnel and achieve what is known as an ALARA dose (as low as is reasonably achievable).

In addition, a fluoroscopy system may include a table on which the patient may be moved relative to the X-ray device. Different motion parameters may be provided for the various movements. In particular, the table may be moved by a motor. If applicable, it may be moved freely at least in one plane, for instance, using a joystick. In some cases, the movements may be performed at different speeds. Tables are also known, however, that may be moved manually in all directions once a brake is released.

In medical systems, anatomical data may also be available during operation. Anatomical data may relate to regions of the body that are currently undergoing a fluoroscopic examination. So, for instance, latest anatomical data may relate to the heart or a cardiac region, to the spine or a spinal region or to limbs or a limb region.

SUMMARY AND DESCRIPTION

The scope of the present disclosure is defined solely by the appended claims and is not affected to any degree by the statements within this description. The present embodiments may obviate one or more of the drawbacks or limitations in the related art.

The object of the present disclosure is to improve and/or simplify the operation of a medical system.

A method for operating a medical system is hence provided, in which a patient is moved relative to a component of the system, or the component is moved relative to the patient, according to a motion parameter. The medical system may include an imaging system and a table on which a patient may be positioned. The patient on the table may be moved relative to the imaging system for the examination by the imaging system. The movement of the patient by the table, or else the movement of the imaging system with patient stationary, may be characterized by one or more motion parameters.

In addition, the medical system may be defined by one or more additional process parameters during operation. This one process parameter or the plurality of process parameters differ from the one motion parameter or the plurality of motion parameters. Thus, there exist a parameter pair, parameter triple, and so on. The motion parameters and similarly the process parameters may assume different values. However, not all the combinations of parameter values may make sense for operation. For instance, when there is a high zoom factor, it makes no sense to allow a high speed between the components being moved towards one another. It makes just as little sense when travel speeds are high to set high X-ray doses for high image quality. Therefore, the motion parameter interacts automatically with another process parameter of the medical system so that a value of the process parameter changes dynamically with a value of the motion parameter. Thus, a motion parameter is coupled to another parameter of the medical system, which parameter is independent of the movement and/or has no effect thereon. It is hence possible specifically to avoid process-parameter/motion-parameter combinations that make no sense. It may be the case here that the process parameter is selected and the motion parameter is altered automatically accordingly. Conversely, however, it may also be the case that the motion parameter is specified and the process parameter is adapted dynamically.

The motion parameter may be a speed or an acceleration. In principle, however, the motion parameter may also define a direction, a jolt, or the like. In particular, for instance, the motion parameter may therefore relate to a motor speed of a table of the medical system.

Thus, in a particular embodiment, a motor drive may be provided in the medical system in which the speed is altered automatically according to the process parameter. Hence, for example, for a first process parameter, the motor drive is set automatically to a first speed, and for a second process parameter, is set automatically to a second speed. Thus, for instance, in a specific operating phase or in a specific process, the patient table may be moved only at a first speed, and in a second operating phase or in a second process, only at a second speed.

It may be provided in another embodiment that the medical system has a table that may be moved manually or another component that may be moved manually. It may be provided here that friction for a negative acceleration is set automatically according to the process parameter. This may mean that control of a friction brake is directly dependent on a process parameter. Thus, for instance, a high friction may be set if it makes more sense, for example, to move the table only at slow speeds. On the other hand, the friction brake may be automatically released fully, for example, if high speeds are actually permitted or sensible in a process (for instance, the automatic movement of the patient out of the fluoroscopy region).

The process parameter may be an image parameter of the component, which is embodied as an imaging apparatus. The process parameter thus relates to an image attribute of the imaging apparatus. In this case, an image parameter of the medical system is coupled to a motion parameter of the medical system. Hence in particular the image quality and/or quantity may be made dependent on the movement.

According to one embodiment, the image parameter is a radiation intensity, an X-ray dose, a gain factor, or a zoom factor. For instance, it is necessary or sensible to reduce the radiation intensity or X-ray dose when the patient is being moved at a high speed. This is because, at a high speed, it may be sufficient to obtain images at low resolution, for instance to get to the required position. Once the destination is reached, then the speed may be reduced (e.g., possibly down to 0) and a high image quality is desired. In this case, at low speed the radiation intensity or the X-ray dose may be increased again.

In another example, a high zoom factor may be selected. In this case, it is not desirable for the patient to be moved rapidly under the imaging apparatus because orientation may quickly be lost as a result of the high magnification. Indeed, at high magnification, the images move correspondingly faster on the screen.

In another embodiment, the process parameters may contain anatomical data. For instance, the anatomical data may contain information about the region of the body from which a displayed acquisition or the segment undergoing fluoroscopic examination originates. For instance, it may be advantageous to allow higher speeds for a certain tissue type than for another tissue type.

In addition, it may be provided that the value of the process parameter is altered by a fixed value if the value of the motion parameter exceeds a predetermined value. If the speed at which the patient is moved relative to the component of the medical system is greater than a predetermined speed, then, for example, the process parameter is reduced by one level, halved, or otherwise altered incrementally. It may be advantageous, for example, to set the zoom factor to the smallest level if a certain speed of the patient is exceeded.

It may be provided in a development that the value of the process parameter is altered continuously with the motion parameter. Thus, in this case, the value of the process parameter is not altered incrementally but in an infinitely variable, (e.g., continuous), manner. Thus, for example, there may be a linear, square, exponential, or other continuous relationship between the process parameter and the motion parameter.

The aforementioned object is also achieved by a medical system including a component and a movement apparatus that may be used to move a patient relative to the component, or move the component relative to the patient, according to a motion parameter. The medical system also includes a controller, which allows the motion parameter to interact automatically with another process parameter of the medical system so that a value of the process parameter changes dynamically with a value of the motion parameter.

The advantages and possible developments mentioned in connection with the method may also be applied mutatis mutandis to the medical system. The individual method acts are thereby regarded as functional features of suitable components of the medical system (e.g., movement apparatus, controller, and the like).

In a specific embodiment, the component may be an X-ray device, and in particular, a C-arm X-ray device. Thus, the patient is moved relative to the X-ray device. The movement, for example, is an angulation of the C-arm X-ray device. A parameter concerning this movement is then made dependent on another process parameter, which, in particular, is an image parameter of the X-ray device.

It may be provided in another embodiment that the medical system has a table on which the patient may be moved manually or by a motor. In particular, the table may be an operating table. If the patient, or more specifically the operating table, may be moved manually, the friction of a friction brake may be increased automatically when the zoom factor of the imaging X-ray device is high. Thus, for instance, the friction may be increased linearly with the zoom factor. When the table is pushed manually, the operator has to overcome a higher resistance in order to move the table.

BRIEF DESCRIPTION OF THE DRAWINGS

The present disclosure is now explained in more detail with reference to the accompanying drawings, in which.

DETAILED DESCRIPTION

The exemplary embodiments described in greater detail below constitute embodiments of the present disclosure. It should be noted that the individual features may be implemented not only in their described feature combinations but also in isolation or in other technically practical combinations.

The fundamental idea is based on adapting an operating parameter during operation in order to achieve improved utilization and in particular for medical imaging equipment, to minimize the radiation dose.

Figure 1:
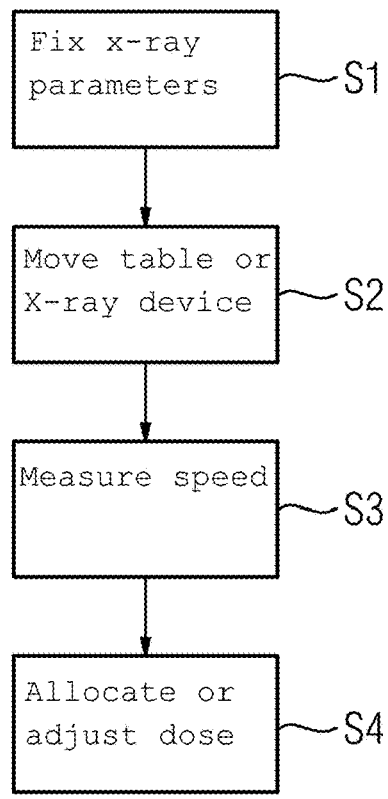
FIG. 1 depicts a flow diagram of a method according to a first exemplary embodiment.

In the example of FIG. 1, the radiation dose is reduced during a movement of the patient relative to the acquisition apparatus, in other words relative to a component of the medical system. Specifically, for example, the X-ray parameters in an angioscopy system are fixed for optimum image quality for an ALARA dose for a non-moving system, in accordance with act S1. Then, for example, the table on which the patient is located, or the C-arm of the X-ray device, is moved during an acquisition or fluoroscopy examination, in accordance with act S2. The patient consequently moves relative to a component of the medical system or of the X-ray device. Conventionally, the image quality would be left unchanged at high during the movement, even though this is not necessary from the user viewpoint. It would be acceptable to reduce the dose during the movement (e.g., and then raise it again), because the human eye may not resolve the full image quality during the movement.

The movement of the table in accordance with act S2 is performed either by motor or manually. For movement by motor, the speed of the table is normally also known directly. A corresponding speed value of the "speed" motion parameter may be provided by the system. If, however, the table is moved manually, the speed of the table is not directly available. Instead in this case, the speed is measured in accordance with act S3. A suitable sensor in the medical system thus detects the speed of the patient relative to a component of the medical system (e.g., X-ray detector). In a subsequent act S4, the dose is allocated or adjusted according to the motion parameter. The allocation or adjustment may be made in increments or continuously. For instance, the higher the detected speed between patient and acquisition apparatus, the further the radiation dose is reduced.

For example, a dose is reduced automatically during an image acquisition or fluoroscopic examination when the patient table or the C-arm is brought into a different position. This results in a slightly lower image quality during the movement. Simultaneously, however, the dose to the patient and to the personnel is also reduced without impairing the medical results.

Setting a reduced dose, or increasing the detector gain, when the system is being moved reduces the total exposure of the patient during the fluoroscopy examination. In this case, the dose reduction may be achieved solely by decreasing the radiation by a fixed factor or amount. For instance, the radiation dose is automatically decreased to half during a movement of the system. It is also possible, however, to select the dose reduction factor to be directly dependent on the speed value of the movement. The faster the movement, the fewer the details that may be resolved by the human eye, and the greater the dose reduction that may be achieved. Thus, for instance, in angiography procedures, a significantly lower dose may be achieved compared with known systems.

Figure 2:
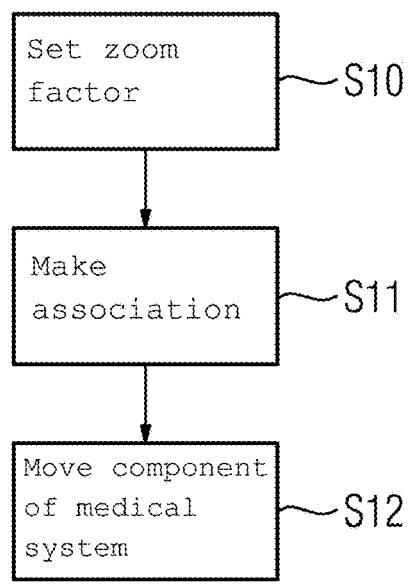
FIG. 2 depicts a flow diagram of a method according to a second exemplary embodiment.

In another exemplary embodiment, depicted in FIG. 2, the movement speed or the system feedback is configured according to imaging settings. In conventional systems from the prior art, a system movement speed or a force for a manual movement, etc., is defined independently of other settings. A known problem, for example, is the precise positioning of the table or of the C-arm of an angiography system during an X-ray procedure when a high zoom factor is set. A suitable setting depends largely on the experience and knowledge of the user. It is therefore proposed to adapt the forces necessary for the manual movement of the system, or the speed of a motorized movement of the system, on the basis of, for instance, the zoom factor setting or another parameter. For instance, the other parameter may be the SID (source-image distance) or the angulation.

The force with which a table may be moved manually may be achieved by adjusting automatically the friction force of a brake fitted to the table. Adapting the speed of a motorized movement may be achieved by appropriate control of the motor used. Adapting the speed results in a selected sensitivity that allows more precise positioning of the system.

To give a specific example, a zoom factor is thus set in accordance with act S10, as shown schematically in FIG. 2 in a flow diagram. In a subsequent act S11, an association is made, for example, between the zoom factor and a maximum speed or a friction, said friction controlling the acceleration. Finally, in accordance with act S12, the table or another component of the medical system is moved at a speed that does not exceed the maximum speed.

Thus specifically, depending on a process parameter such as the zoom factor, SID (e.g., magnification), angulation, or anatomical data in a medical system, the sensitivity of the movement may be adapted by slowing down or speeding up motorized movements and/or, for manual movements, by adjusting the friction. Thus, for instance, if the imaging relates to an anatomical region or a specific process requiring finer adjustment (e.g., neurosurgery or spinal surgery), then this may be achieved automatically by the relevant process parameters. A floating table top of an operating table may thereby be positioned very precisely during an X-ray examination.

Figure 3:
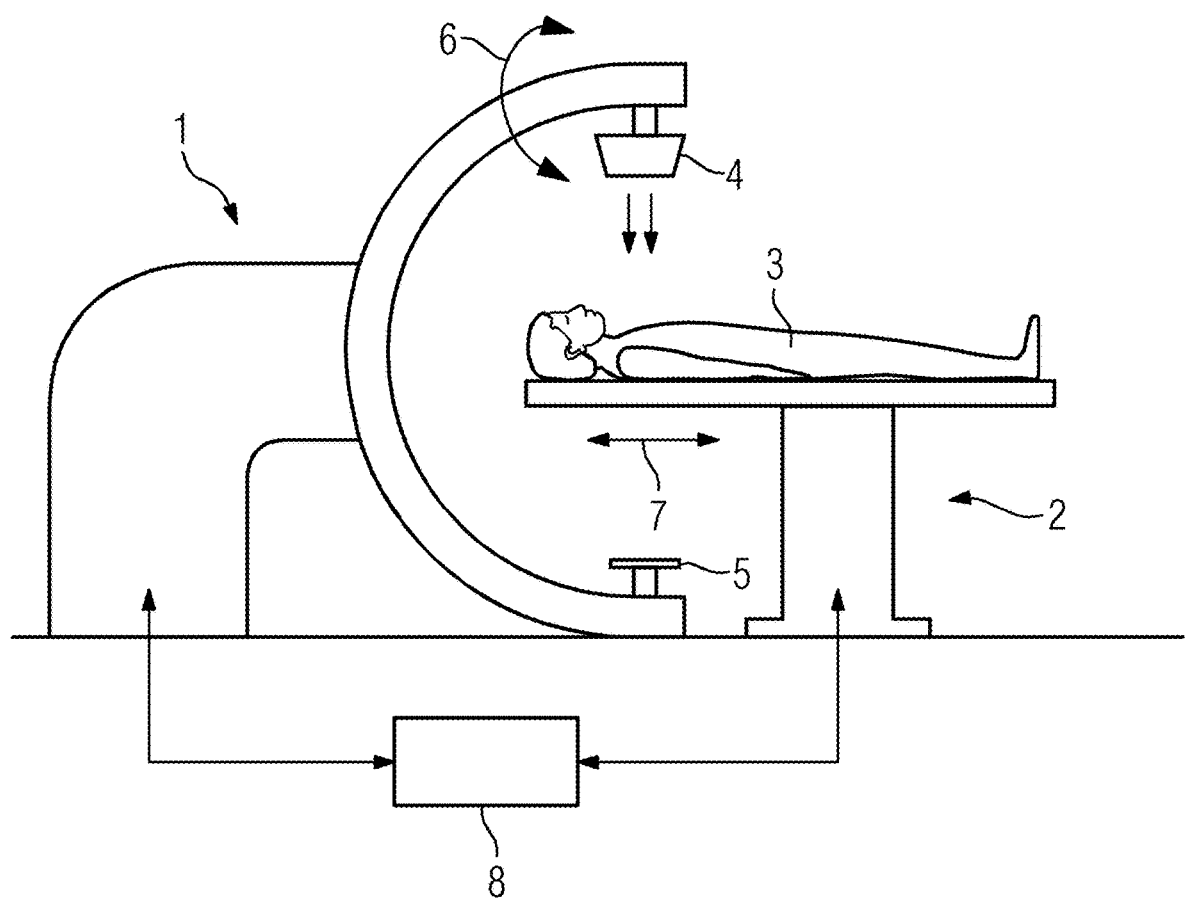
FIG. 3 depicts a schematic diagram of an X-ray system according to an exemplary embodiment.

FIG. 3 depicts schematically a medical system having a C-arm X-ray device 1 and a patient table 2, on which a patient 3 is located. The C-arm X-ray device 1 has at the distal end of the C-arm an X-ray radiation source 4 and opposite a detector 5. The C-arm may be moved and/or pivoted relative to the patient 3 by angulation 6. In addition, the C-arm may have further degrees of freedom of movement. The patient table 2 also allows table movements 7 mainly in one plane, but also perpendicular thereto.

The medical system shown in FIG. 3 thus has a component (e.g., detector 5), with respect to which the patient 3 may be moved relative to the component according to a motion parameter by a movement apparatus (e.g., integrated in the patient table 2 or the C-arm X-ray device 1). In addition, the medical system has a controller 8, which provides an interaction of the motion parameter with another process parameter of the medical apparatus. In particular, a value of the process parameter (e.g., image parameter such as X-ray dose) may change dynamically with a value of the motion parameter (e.g., movement speed of the patient table 2). The controller may also be integrated, for example, in the C-arm X-ray device 1 or the patient table 2.

In a specific example, a catheter is inserted into the patient 3. During the insertion, the position of the patient is tracked in such a way that the catheter tip lies in the acquisition region of the detector 5. Because the patient table 2 is moving, the radiation dose is decreased during this movement by a fixed value or by a value that corresponds to the speed. The total dose for the patient may thereby be reduced during the operation, for example, to 80 percent or another value.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical system, the method comprising:
   setting a radiation dose for a patient for an examination;
   moving, according to a motion parameter, the patient relative to an imaging apparatus of the medical system or the imaging apparatus of the medical system relative to the patient, wherein the motion parameter is a speed or acceleration of a table on which the patient is positioned or a position of the imaging apparatus relative to the patient; and
   dynamically changing a value of the radiation dose based on a value of the motion parameter, wherein the motion parameter interacts automatically with the radiation dose of the medical system such that an increase in the speed or the acceleration of the table or a repositioning of the imaging apparatus relative to the patient results in a reduction in the value of the radiation dose to reduce a total exposure of the patient during the examination.

2. The method of claim 1, wherein a motor drive alters the speed automatically according to the radiation dose.

3. The method of claim 1, wherein friction for a negative acceleration is adjusted automatically according to the radiation dose.

4. The method of claim 1, wherein the value of the radiation dose is altered by a fixed value when the value of the motion parameter exceeds a predetermined value.

5. The method of claim 1, wherein the value of the radiation dose is altered continuously with the motion parameter.

6. The method of claim 1, wherein the imaging apparatus is an X-ray device.

7. The method of claim 6, wherein the X-ray device is a C-arm X-ray device.

8. The method of claim 1, wherein a decrease in the speed or the acceleration of the table or the repositioning of the imaging apparatus relative to the patient results in an increase in the value of the radiation dose.

9. The method of claim 1, wherein the table is moved manually by an operator, and the imaging apparatus dynamically changes the value of the radiation dose based on the movement of the table.

10. A medical system comprising:
    an imaging apparatus;
    a movement apparatus configured to move a patient relative to the imaging apparatus or the imaging apparatus relative to the patient, according to a motion parameter, wherein the motion parameter is a speed or acceleration of a table on which the patient is positioned or a position of the imaging apparatus relative to the patient; and
    a controller configured to allow the motion parameter to interact automatically with a a radiation dose so that a value of the radiation dose changes dynamically with a value of the motion parameter such that an increase in the speed or the acceleration of the table or a repositioning of the imaging apparatus relative to the patient results in a reduction in the value of the radiation dose to reduce a total exposure of the patient during an examination of the patient.

11. The medical system of claim 10, wherein the imaging apparatus is an X-ray device.

12. The medical system of claim 11, wherein the X-ray device is a C-arm X-ray device.

13. The medical system of claim 12, further comprising:
    the table on which the patient is configured to be moved manually or by a motor.

14. The medical system of claim 10, further comprising:
    the table on which the patient is configured to be moved manually.

15. A method for operating a medical system, the method comprising:
    moving, according to a motion parameter, a patient relative to an imaging apparatus of the medical system or the imaging apparatus of the medical system relative to the patient; and
    dynamically changing a value of a process parameter based on a value of the motion parameter, wherein the motion parameter interacts automatically with the process parameter of the medical system,
    wherein the process parameter comprises an image parameter of the imaging apparatus of the medical system,
    wherein the image parameter is a gain factor or a zoom factor.

16. The method of claim 15, wherein the process parameter further comprises anatomical data of the patient.

17. The method of claim 16, wherein the anatomical data is a tissue type of the patient.

* * * * *